United States Patent [19]

Morris

[11] Patent Number: 4,982,732
[45] Date of Patent: Jan. 8, 1991

[54] ORTHOPEDIC REHABILITATION KNEE BRACE

[75] Inventor: John C. Morris, Castro Valley, Calif.

[73] Assignee: Orthopedic Technology, Inc., San Leandro, Calif.

[21] Appl. No.: 475,571

[22] Filed: Feb. 6, 1990

[51] Int. Cl.⁵ .................................................. A61F 3/00
[52] U.S. Cl. ................................ 128/80 C; 128/80 R; 128/77; 128/80 H; 403/96
[58] Field of Search .................. 128/80 R, 80 C, 80 F, 128/80 H, 77; 623/39, 40, 41, 42, 43, 44, 45, 46, 60; 403/92, 93, 95, 96

[56] References Cited

U.S. PATENT DOCUMENTS

| | | | |
|---|---|---|---|
| 2,770,811 | 11/1956 | Steeper | 623/39 |
| 4,340,041 | 7/1982 | Frank | 128/80 C |
| 4,407,276 | 10/1983 | Bledsoe . | |
| 4,489,718 | 12/1984 | Martin . | |
| 4,620,532 | 11/1986 | Houswerth | 128/80 F |
| 4,817,588 | 4/1989 | Bledsoe . | |
| 4,846,842 | 7/1989 | Connelly et al. | 128/80 C |

Primary Examiner—Richard J. Apley
Assistant Examiner—Lynne A. Reichard
Attorney, Agent, or Firm—Townsend and Townsend

[57] ABSTRACT

An orthopedic rehabilitation knee brace having paired labeled hinges on either side of a braced knee is provided with easily set flexion and extension limits of movement for providing to the braced leg limited post-operative or recovery restraint of the knee. Each brace includes two improved circular hinge elements with a first group of easily set stops for producing restraint in flexion and a second group of easily set stops for producing restraint in extension of the knee. Extending upwardly and downwardly from each circular hinge housing on both sides of the brace are telescoping respective upper and lower leg wings for effecting from the hinge desired restricted movement of the leg member at the knee joint. The discrete flexion and extension stops extend radially of the hinge and are normally in the disengaged position. Each of the individual stops is exposed through the outward portion of the hinge for manipulation at attached stop operating points. These operating points act as indicators in the radially out position for the limits of movement of hinge setting. The individual stops each act on a detent. The mechanism locks all detents commonly to secure flexion and extension settings of the hinge. Provision is made for providing locking and unlocking of the stops at their detent through a keyed wrench so that the brace can be locked against patient or bystander tampering after setting.

18 Claims, 8 Drawing Sheets

ORTHOPEDIC REHABILITATION KNEE BRACE

BACKGROUND OF THE INVENTION

1. Field of the Invention

This invention relates to therapeutic knee braces. More particularly, an improved hinge element is disclosed for use on both sides of an orthopedic rehabilitation knee brace. The improved hinge is characterized by labeled, easily set and easily locked flexion and extension stops for post-operative or recovery bracing of the knee with restraint of knee movement.

Statement of the Problem

Therapeutic knee braces are commonly installed on the operating table after knee surgery or alternately after an injury to the knee. Such braces are maintained on the knee for two purposes. First, the braces have the purpose of bracing the knee during movement. Second, the braces are present to limit knee movement in flexion or extension beyond limits where reinjury to the knee may occur.

For the most part, knee braces satisfactorily reinforce the knee during movement. It is in the limitation of knee movement that problems occur.

It is first and foremost required that such braces be capable of being adjustable within limits required for the healing restraint of the patient's knee. Limits used are both in flexion and extension.

Flexion is designated as flexing of the knee from the extended position to the position where the foot and ankle comes under the buttock. Extension is a term applied to the opposite movement. The extended leg is straight with virtually no bending at the knee joint.

On a post-operative or rehabilitation application, a therapeutic knee joint must be capable of being rapidly set to given limits of both flexion and extension. Such setting should preferably occur at the time of brace installation. It would be preferred if setting could occur with minimum usage of special tools or manipulation.

Second, knee braces once set should be reasonably free from patient or bystander tampering. That is to say, once the hinge of such a brace is set for limits of flexion or extension, changing of the setting should only occur under deliberate alteration, either personally by the physician or therapist or at the instruction of the physician or therapist.

It goes without saying that such braces should be readily adjustable responsive to sensory input from the patient. Typically and during the recovery process, patients are frequently asked to flex a knee being rehabilitated until some discomfort is noted. When the discomfort occurs, there is a need to set the brace to that degree of flexion or extension required for rehabilitation without further "testing" of the limits of movement of the recovering knee joint.

2. Brief Description of the Relevant Art

Bledsoe U.S. Pat. No. 4,817,588 is exemplary of prior art knee braces and includes paired hinge members limiting flexion with straps limiting extension. The disclosed hinge has a single adjustable dial that cooperates with a pair of stop members to selectively limit the relative pivotal movement between the thigh and calf supporting members associated with the hinge.

Bledsoe U.S. Pat. No. 4,407,276 is an example of a knee brace the purpose of which is for reinforcement of the knee joint. Limitations of movement are not provided by the hinge members.

It is known to provide a knee brace having paired hinge members, which hinge members are restricted in movement with respect to flexion and extension. Typically, such limits of movements are established by applying to the brace individual screws or pins.

Martin U.S. Pat. No. 4,489,718 is an example of a knee brace hinge wherein the restraints in flexion and extension are set by a threaded member, in this case a coil, to set the limits of hinge movement.

SUMMARY OF THE INVENTION

An orthopedic rehabilitation knee brace having labeled and easily set flexion and extension stops for post-operative or recovery restraint of the knee is disclosed. The brace includes two hinge members on both sides of the knee. Each hinge member is an improved circular hinge element with a first set of stops for producing restraint in knee flexion and a second set of stops for producing restraint in knee extension. Extending upwardly and downwardly from the circular hinge housing on both sides of the brace from both hinges are respective upper and lower telescoping wings for desired restriction of the calf and thigh portions of the leg from the paired hinge members on either side of the knee joint.

Each hinge member includes a circular housing with discrete stops at 10° intervals. The discrete stops are positioned radially of the hinge and are normally in a radially inward disengaged position. There are 16 radial stops for restricting extension for a total extension adjustment of 150°. There are 16 radially extending stops for restricting flexion at 10° increments for 150°.

Each of the individual stops is exposed for manipulation at attached stop operating points. Stop operating points extend through slots in the cover of the hinge members and are exposed to the outside surface of the knee. The slots and operating points act as indicators displaying to the party setting the hinge the respective values of flexion and extension for any individual hinge setting.

The discrete stops move between an engaged and disengaged position at a detent point on the stop acting against a radial leaf spring. The radial leaf spring is backed by a stop retaining locking ring. When the stop retaining locking ring is moved away from the radial leaf spring, movement of the stops can occur. When the stop retaining locking ring is pressed against the radial leaf spring, movement of the stops at their detents is inhibited and the hinge is locked in its setting.

In operation and before application of the brace, full movement in the extension and flexion of the hinge elements is provided by backing the stop retaining rings away from the spring and moving the stops to the retracted position. Thereafter, manipulation of the hinge stops occurs with setting of the hinge to the desired value of flexion and extension. Alternately, manual manipulation of the braced knee can occur to the desired range of movement, this movement being indicated by gun sight markings on the hinged sidewalls opposite the respective values of flexion and extension. Individual stops are set. After setting of the individual stops, the stop retaining locking ring is tightened onto the leaf spring assembly. Manipulation of the hinge stops is not possible and the hinge members are set at their desired value of flexion and extension. Setting of the stop retaining locking ring can be provided through a keyed wrench so that the brace can be locked against patient or bystander tampering.

Other Objects, Features and Advantages

An object to this invention is to disclose an improved joint for a knee brace which is simply set in both values of extension and flexion. Accordingly, 16 stops are radially aligned at 10° increments for adjustment of extension. Similarly, 16 radially aligned stops at 10° intervals are adjustable for flexion. Normally all stops—except those at the ends of limit of travel—are in the retracted radially inward position. Each stop has a protruding operating point exposed to the exterior of the hinge through an appropriate labeled slot. By the expedient of manipulating the stop at the operating point, desired values of flexion and extension are both set and indicated exteriorly of the hinge.

An advantage of the exposed operating points of the stops is that they are easily manipulated externally of the hinge and provide indicators of hinge movement which can be quickly read. Further, the stops can be moved with any relatively pointed implement including a ballpoint pen, a safety pin, a pencil, or any other pointed object capable of fitting into the radially aligned slots and exerting a minimum force to overcome the detent mechanism.

An advantage of the labeled radially arrayed stops and their protruding operating points is that brace adjustment during rehabilitation can occur both to arbitrary chosen limits and responsive to patient indication of the onset of physical discomfort due to knee movement. According to this aspect, the improved hinge of this brace is provided on the exterior of the body of the hinge with an indicator for both flexion and extension. This indicator can be utilized with the radially aligned and labeled stops for rapid setting of the brace. For example, the patient can be asked to carefully flex the unrestrained and recovering knee joint. The attending physician or therapist can readily observe the coincident of the hinge indicator at a labeled radial slot. The degree of limb movement needed to permit recovery with minimum discomfort and maximum therapeutic effect can be rapidly set on the hinge.

A further object to this invention is to disclose numerous stops which can be readily and individually manipulated during adjustment but which can be easily locked during normal knee brace operation.

According to this aspect each of the stops is equipped with a detent. The detent is backed by a spring leaf from a radial leaf spring assembly. The radial leaf spring is in turn backed by a stop retaining locking ring. This stop retaining locking ring moves between a position where all stops are restrained from motion by their detent to a position where all stops can be toggled between a hinge restraining position and a normally open position.

An advantage of this aspect of the invention is that movement of the hinge from the adjustable format to the locked format is simply accomplished by tightening of the stop retaining locking ring against the radial leaf spring. Thus, the hinge, when set to the desired limits of motion, enables convenient locking of all of the individually adjustable stops.

The further advantage of this invention is that the tightening of the stop retaining locking ring can be restricted to an especially constructed tool. With this especially constructed tool, a compliance lock inhibits patient or bystander tampering with the adjusted hinge It will be understood that it is not the purpose of this invention to render the hinge settings tamper proof. It is the purpose of this invention to make such tampering inconvenient so that only deliberate action can change hinge adjustment.

DETAILED DESCRIPTION OF THE DRAWINGS

Other objects, features and advantages of this invention will become more apparent after referring to the following specification and attached drawings in which.

Figure 1:
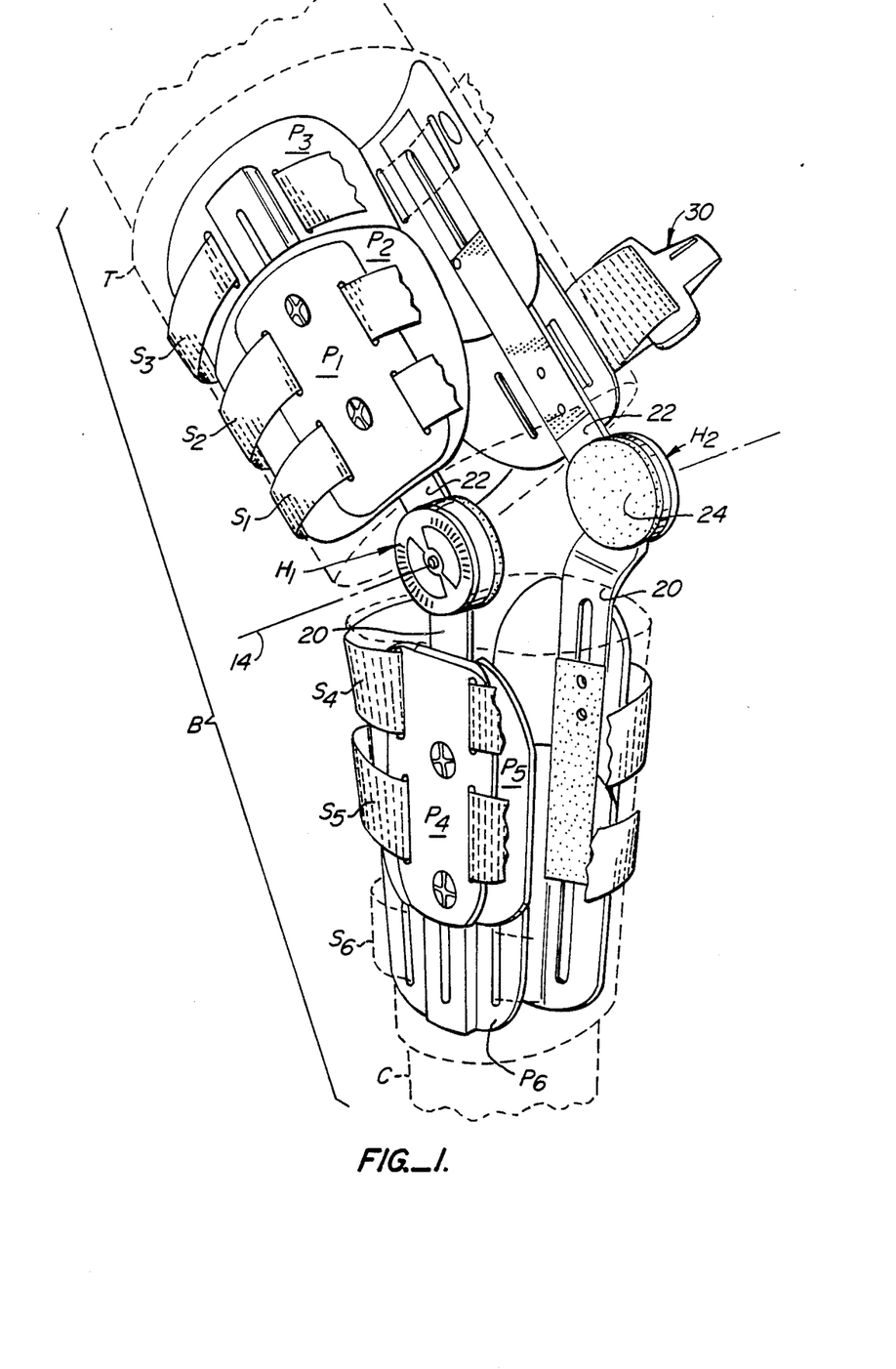
FIG. 1 is a perspective of the knee brace of this invention shown in a disposition for clamping a knee, with only portions of the braced thigh and calf being illustrated in broken lines.

Referring to FIG. 1, a knee brace B is shown in perspective bracing a calf C and a thigh T at the knee joint (the knee not being shown). Typically, two hinge elements $H_1$ and $H_2$ operate to effect the desired bracing of the knee. These respective hinge elements perform two functions.

Similarly to a normal knee, the hinge elements $H_1$, $H_2$, along their respective axis 14 enable the knee to be therapeutically reinforced as the knee bends. Thus, bending with the weight of the body between the thigh T and the calf C occurs with part of the stress being delivered through the respective hinge joints $H_1$ and $H_2$.

Second, the hinge joints $H_1$ and $H_2$ each serve to restrict the degree of movement permitted between the thigh T and the calf C at the knee joint coincident to axis 14. It is this restriction of motion that constitutes the primary purpose of this invention.

Referring further to FIG. 1 it can be seen that hinge element $H_2$ is connected to a calf strut 20 and to a thigh strut 22. A foam rubber pad 24 cushions circular hinge element $H_2$ as it bears against the knee. Hinge $H_1$ is similarly provided. Each thigh link 22 is provided with three wings. As illustrated from hinge member $H_1$ these wings include wing $P_1$, wing $P_2$ and wing $P_3$. As will hereinafter be noted with respect to FIG. 2, the wings $P_1$ and $P_2$ on one hand and pad $P_1$ on the other hand telescope with respect one to another. This telescoping enables the brace of this invention to accommodate long legs as when the wings are extended relative to one another and shorter legs as where the wings are compressed to underlie one another. These wings can also be moved in total to accommodate long or short legs, by sliding along calf strut 20 and thigh strut 22.

Similarly to thigh strut 22, calf strut 20 has three wings $P_4$, $P_5$, $P_6$, telescoping with respect thereto. These strut wings telescope to and from an overlying disposition to accommodate calves of various sizes.

Each of the respective wing members $P_1$, $P_2$ and $P_3$ are of an arcuate profile, semi-rigid and encircled by straps. Specifically, straps $S_1$ and $S_2$ encircle wing members $P_1$ and $P_2$ As indicated, straps $S_1$, $S_2$ are threaded through wing $P_1$ at the side edges of wing $P_1$. Straps $S_1$ and $S_2$ pass around wing member $P_2$. Such threading assures firm bias of the wings $P_1$ and $P_2$ to the thigh. Similarly, a strap $S_3$ secures wing $P_3$. It will be appreciated that should wing $P_6$ be telescoped underlying wing $P_2$, strap $S_3$, may be removed.

Similarly, wing $P_4$ is provided with strap $S_4$ and $S_5$. These straps thread through wing $P_4$ and extend around the side edges of $P_5$ to firmly grip the calf. A strap $S_6$ is here shown in broken lines. For large calves and assuming that wing $P_6$ telescopes outwardly from under wing $P_5$, strap $S_6$ may add to the bracing.

It will be realized that for the comfort of the wearer foam and padding is liberally applied to the respective struts 20, 22 and underneath the respective wings. As this is a matter well within skill of the art it will not be further discussed herein.

Furthermore, buckles 30 may be utilized at the ends of the wings, these buckles permitting tightening of the straps and releasable attachment of the straps and brace. As such buckles are well known in the prior art, they will not be further set forth herein.

Figure 2:
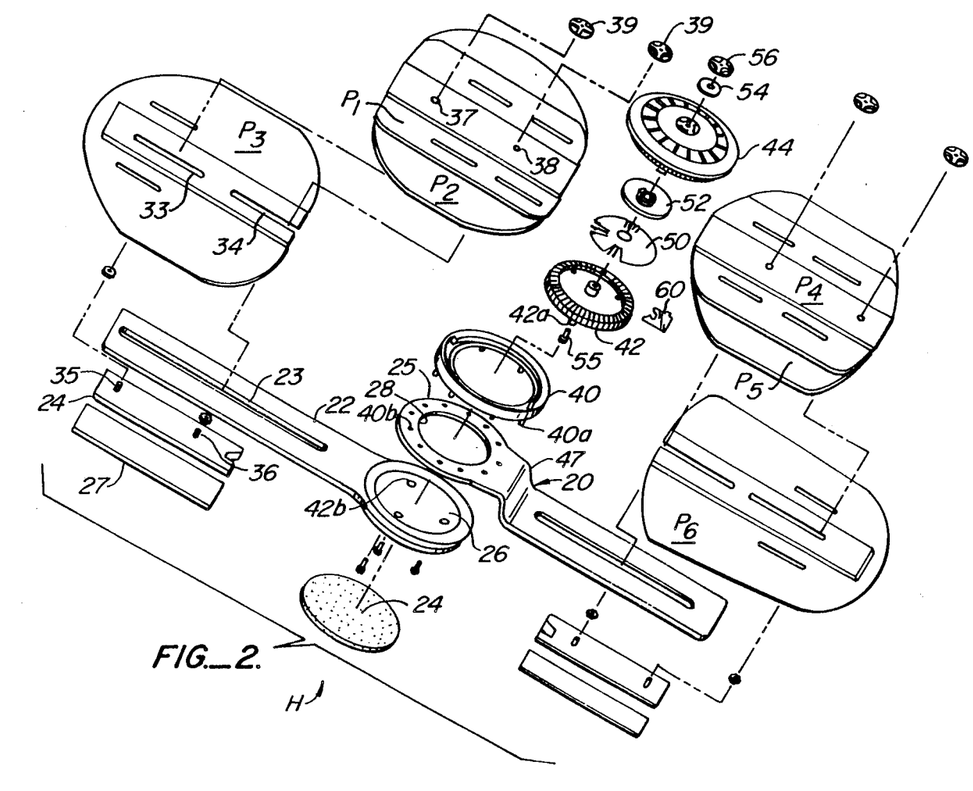
FIG. 2 is an exploded version of one-half of the knee brace, this exploded version disclosing the hinge and wings but only illustrating one stop.

Referring to FIG. 2, and exploded version of a hinge H is illustrated together with the telescoping wings. It will be realized that this assembly is duplicated on both sides of the leg. Telescoping wings will first be described. Thereafter, the exploded components of the hinge will be set forth.

Regarding the wings, it can be seen that thigh strut 22 is provided with an elongate slot 23. It is into this slot 23 at a backing bar 24 covered by a velcro strip 27 there is secured wings $P_3$, $P_1$, and $P_2$. Specifically wing $P_3$ through respective elongate slots 33, 34 moves on respective threaded screws 35, 36 in telescoping relation along slot 23. At the same time the threaded screws 35, 36 enable wings $P_1$ and $P_2$ at apertures 37, 38 to move along the length of the slot 23 in thigh strut 22. As is conventional, fastening of the respective wings $P_2$ and $P_3$ occurs at hand nuts 39. It will therefore be understood that the range of movement of the respective wings $P_1$ and $P_3$ accommodates long and short respective lengths with respect to the exploded hinge member H illustrated in FIG. 2.

As the construction of wings $P_4$, $P_5$, and $P_6$ and their telescoping action with respect to calf link 20 is analogous, construction will not be set forth in detail. It is sufficient to note that bar 20 includes a bend 47 which bend 47 enables the pad $P_4$, $P_5$, $P_6$ to grasp the relatively smaller calf C with respect to the thigh T.

Having set forth the construction of the wing members with respect to FIG. 2, the hinge mechanism can now be discussed in detail.

Calf strut 20 has a cam portion 40 of the hinge fitted thereto. Cam portion 40 is circular and fits at pins 40A into holes 40B in calf strut 20. Cam member 40 forms a portion of the hinge against which stops 60 act. The stops 60 act against an annular cam defined interior of the hinge member 40. This annular cam will be further set forth with respect to FIGS. 3, 5B, and 6B. Calf strut 20 includes a circular aperture 28. It is through this circular aperture 28 that circular hinge member 42 at pins 42A keys to apertures 42B and thigh strut 22. As will hereinafter be explained in more detail, stops 60 key to slots in circular hinge member 42. When the stop abuts an end of the cam at cam member 40, angular motion of thigh link 22 with respect to calf link 20 is halted. Thus, the hinge is given limits of movement provided by stop 60 lodged within member 42. In FIG. 2 only one stop member 60 is disclosed. In actual fact, 32 stop members are utilized For simplicity only one stop member is here illustrated.

Figure 3:
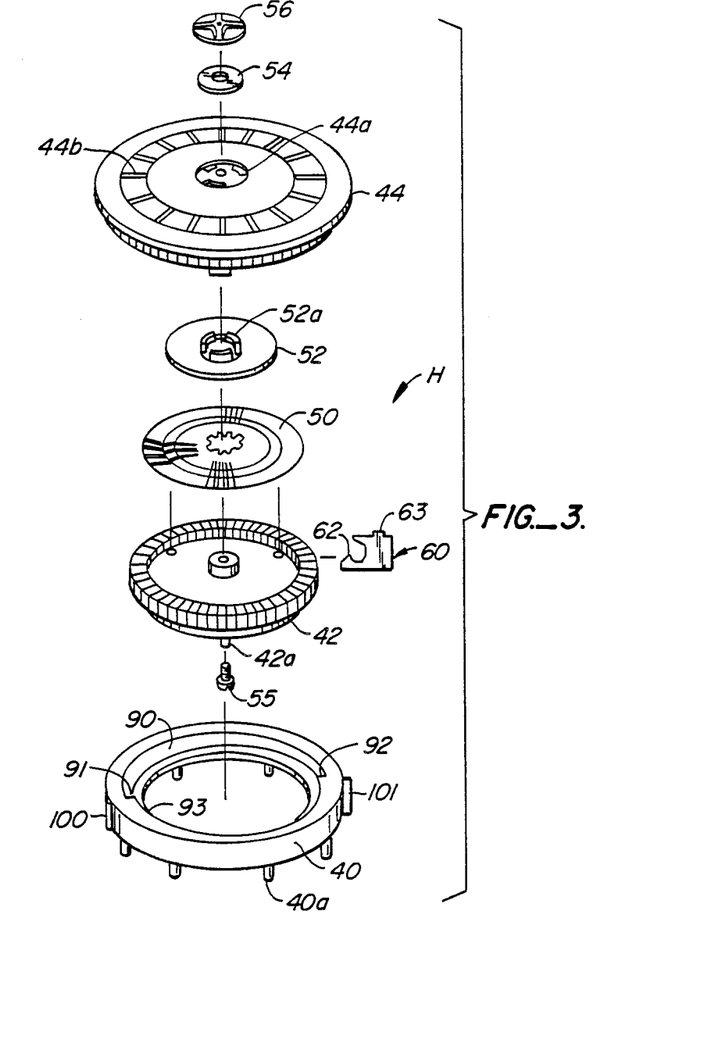
FIG. 3 is an exploded view of the operative portion of one of the hinge elements for the stop.

Referring briefly to FIG. 3, stop 60 includes two active portions. There is a detent portion 62. As will hereinafter be set forth, this detent acting against individual spring leafs of an overlying circular leaf spring 50 enables the stop 60 to toggle. The stop 60 toggles between an inwardly disposed radially disengaged position and an outwardly disposed engaging position. Second, the stop 60 includes an operating portion 63. Operating portion 63 forms two functions.

First, the operating portion permits manipulation of the stop 60 from the exterior of the hinge.

Second, and when the hinge is enclosed, the operating portion 63 acts as an indicator. This indicator displays when the stop is in the engaged position or disengaged position.

Overlying the respective stops is a radial leaf spring assembly having individual leafs for each stop 50. Radial spring 50 bears against the stop 60 at detent 62. This enables toggling of the stop to and from the radially engaging position acting on spring 60.

Overlying spring 50 is a stop retaining ring 52. Stop retaining ring 52 prevents flexing of spring 50 when the ring is engaged firmly over the spring. When the stop retaining ring 52 is given spacing with respect to spring 50, the respective stops 60 may be toggled between their respective engaged and disengaged position.

Overlying the stop retaining ring 52 there is provided a second hinge member 44. Hinge member 44 serves three discrete functions.

First, hinge member 44 captures the stops 60 within the hinge member. It prevents the assembled pieces from becoming disengaged from the hinge.

Second, hinge member 44 provides apertures 44a for compressing the stop locking ring 52 towards and away from the individual stop 60.

Finally, the hinge member 44 includes a number of elongate slots. These respective elongate slots enable the operating portion 63 of the respective slots to be manipulated to move the respective stop 60 between their engaged and disengaged position. At the same time, the operating portions 63 provide indicators of the respective positions, engaged or disengaged, of the respective stops.

Finally in overlying upper hinge member 44 there is provided a bearing washer 54. Bearing washer 54 in combination with screw 55 and bolt 56 enables stop retaining ring 52 to be biased towards and away from the respective stops 60. Tightening of the nut 56 thus can lock or unlock all 32 stops 60 for manipulation in setting the limits of movement of the hinge.

Having explained in a functional and summary fashion the exploded view of FIG. 2, attention will now be directed to the operative portions of the hinge specifically illustrated in FIG. 3.

Referring to the exploded view of FIG. 3, cam portion 40 of the hinge H can be understood. Specifically, an annular cam 90 having respective ends 91, 92 is configured within an otherwise ring-like hinge member. Respective ends of the cam 91, 92 are the members against which stops 60 abut. Stops 60 in their abutment limit the degrees of hinge movement through the respective struts 20, 22 (see FIGS. 1 and 2). A lower continuous annular surface 93 enables smooth rotation of hinge members 42 and 44 relative to cam member 40.

Referring to the stop ring lock 52, it can be seen that upwardly protruding and interrupted flanges 52A are illustrated. Flanges 52A penetrate through apertures 44A and upper hinge member 44. These respected interrupted flanges 52A when acted on by ring 54 under compression from a screw 95 and bolt 56 effect locking and unlocking of the stops 60. When hand nut 56 is tightened, locking occurs. When hand nut 56 is loose, toggling of the respective stops 60 can occur.

The top portion 44 of the hinge also includes radial slots 44B. These respective slots 44B have the operating portion 63 of stop 60 protruding therethrough. Thus, the operating portion 63 can act as an indicator of stop position as well as being directly manipulated by an instrument configured to fit within the slots 44B. Just as there are 32 stops, there are 32 slots configured in top 44. As can be seen, the pictorial representative of FIG. 3 does not include the full number of slots.

Figure 4:
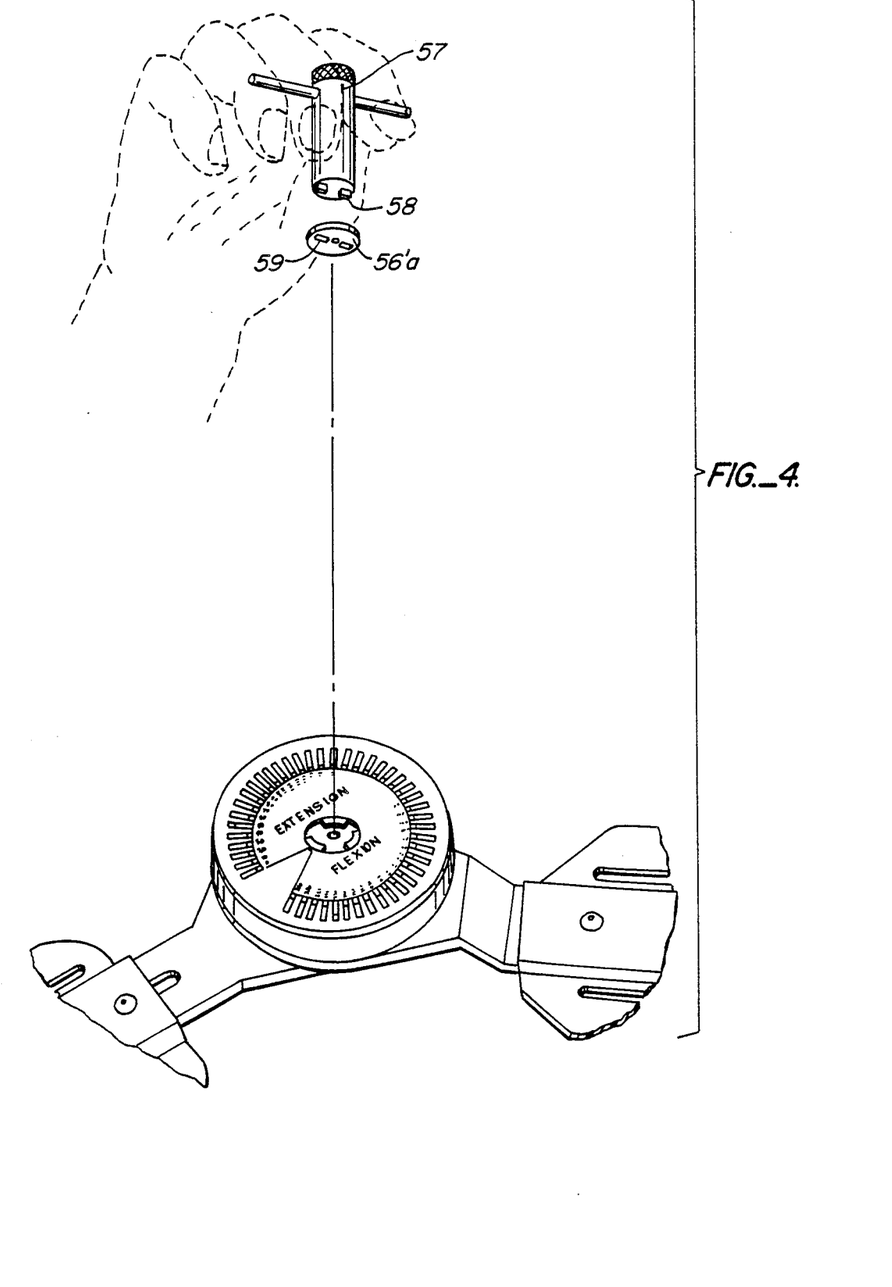
FIG. 4 illustrates a specialized tool used for locking and unlocking the brace.

Referring to FIG. 4, the use of a special tool 57 is illustrated for tightening and loosening the stop locking ring 52. As can be seen, a special key has been utilized having two protruding tangs 58. These protruding tangs 58 fit within complimentary apertures 59' within optional nut 56A. Other keys can likewise be substituted.

The reader will appreciate that such a key inhibits the brace from being inadvertently reset. That is to say, inadvertent adjustment of the device is inhibited. It will be apparent that the device is far from tamper proof. Presumably, most patients will not with deliberation interfere with their rehabilitation.

We have found it preferable to construct the struts 20, 22 of aluminum. The respective hinge pieces 40, 42, 52, 44 are preferably all constructed from fiber reinforced nylon or can be of other high strength materials. The stops 60 are made of hardened steel. It has been found that with this selection of materials which is sufficiently strong for therapeutic purposes a preferred hinge is produced. It is to be understood that these materials do not impart sufficient strength to the brace to make it a so-called "activity" brace. This brace is intended for use in rehabilitation by reasonably careful patients who avoid active physical exercise of the limb.

Figure 5A:
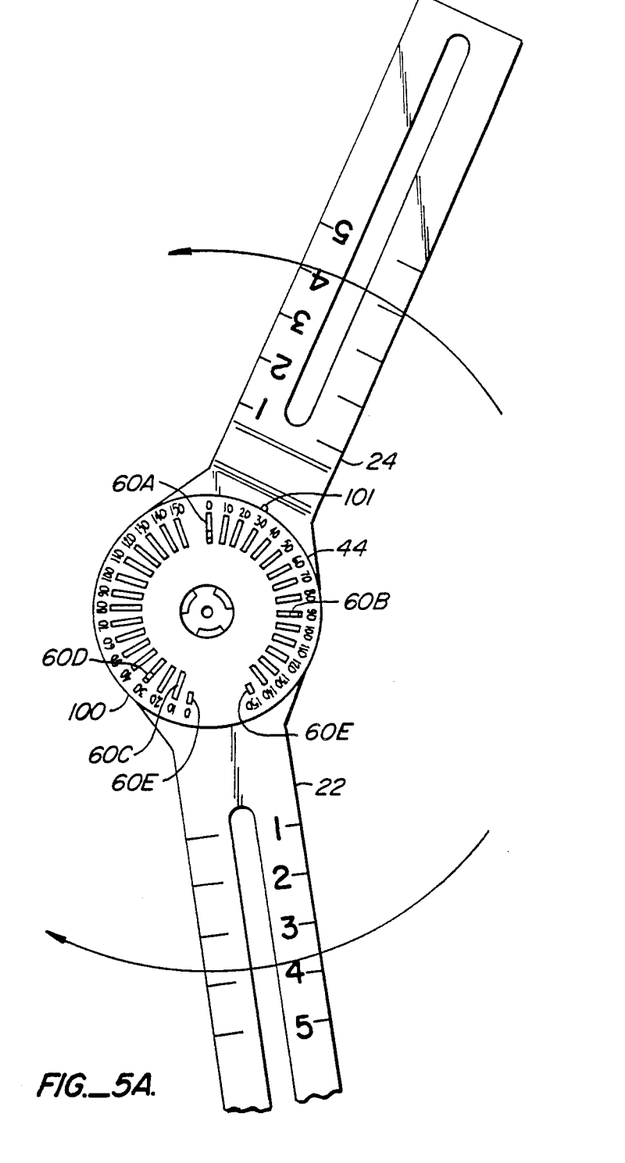
FIG. 5A illustrates a single hinge, the hinge here shown with the cover plate on and manipulated for limiting knee movement to 30° of extension.
Figure 5B:
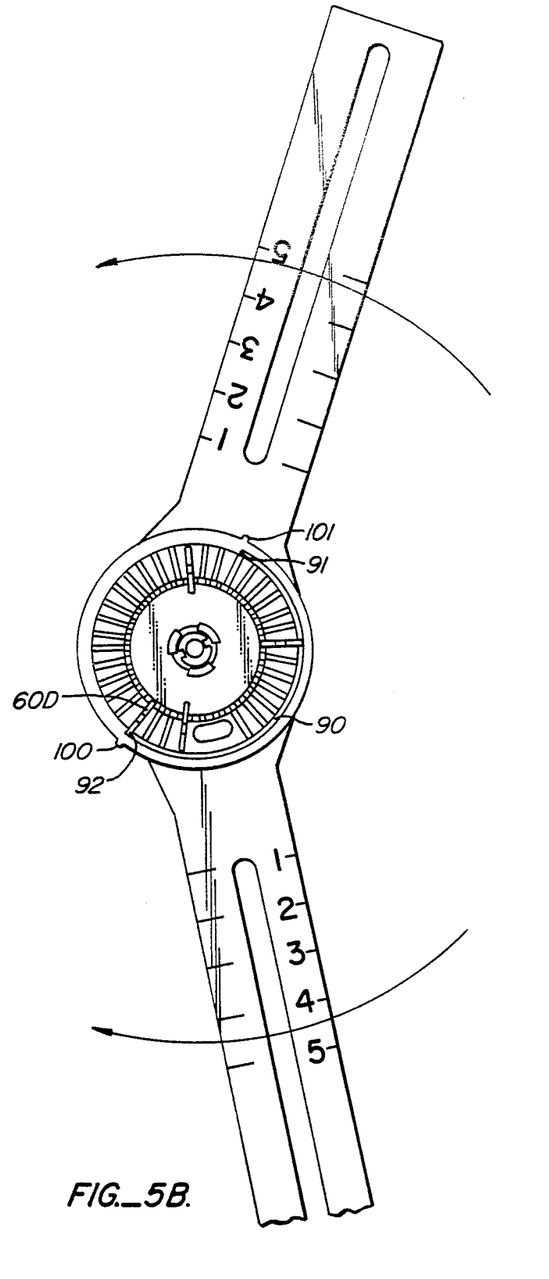
FIG. 5B shows the hinge element of FIG. 5A with the cover removed, this hinge element shown with a stop limiting hinge motion to 30° of extension.
Figure 6A:
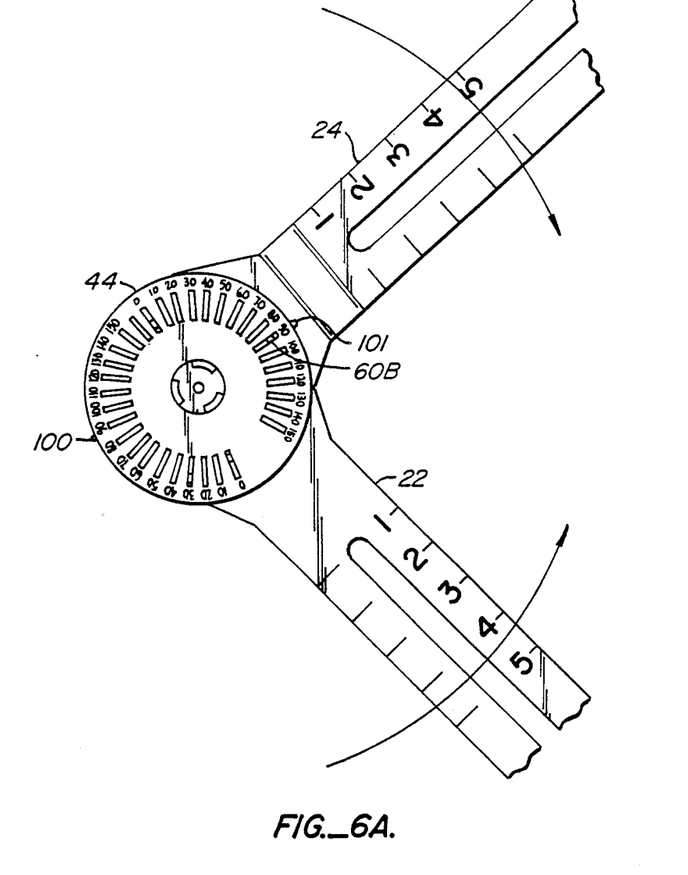
FIG. 6A illustrates the hinge member of FIG. 5A with the knee joint flexed to and limited to 90° of flexion.
Figure 6B:
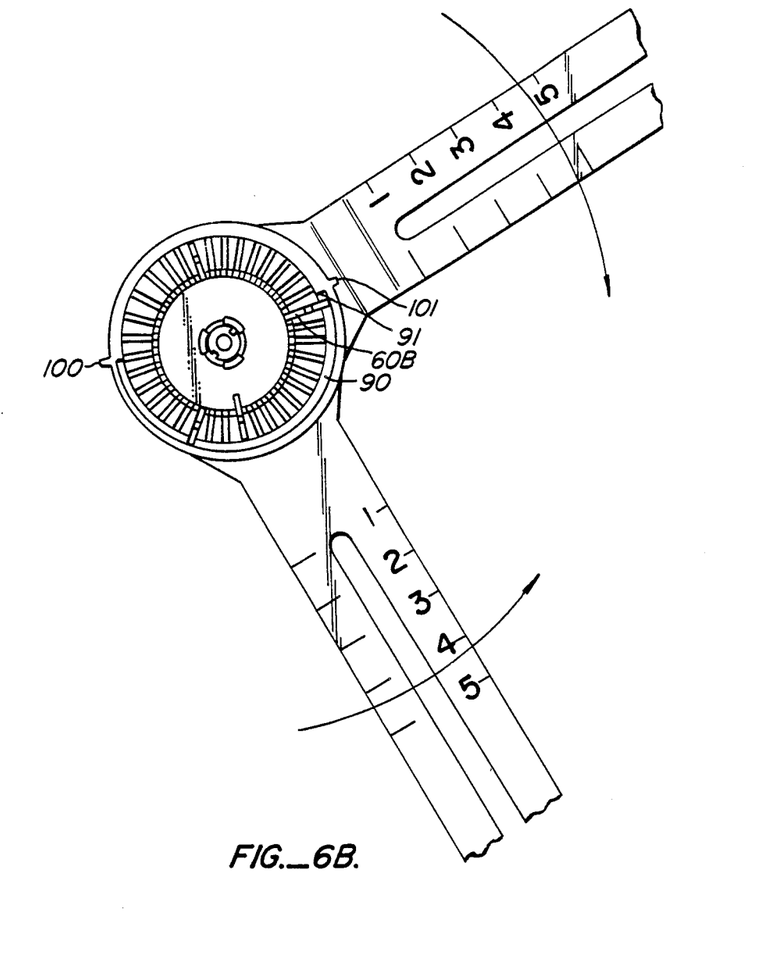
FIG. 6B illustrates the hinge member of FIG. 5B with the cover plate removed and the hinge member limited to 90° of flexion.

Attention will now be directed to FIGS. 5A and 5B for illustrating extension and FIGS. 6A and 6B for illustrating flexion.

Referring to FIG. 5A, the hinge assembly has been partially assembled in accordance with the exploded view of FIGS. 2 and 3. Missing from the hinge assembly are hand nut 56 and bearing washer 54.

In the normal construction of a hinge assembly, some 32 stops are present. In the view of FIG. 5A, two of these stops 60E are immovable in the engaged position so as to prevent missetting of stops beyond a position which would result in injury to the knee. Of the other 30 stops only two stops are utilized. These stops are flexion stop at the 0° position 60A in the disengaged position and flexion stop 60B at the 90° position in the engaged disposition. Likewise, two extension stops are illustrated. These stops are extension stop 60C in the disengaged position and extension stop 60D in the engaged position.

It can be seen that the two struts 22, 24 have been moved to the extended position for realigning the full extension that the brace permits.

Referring to FIG. 5B, piece 44 has been removed. Removal of piece 44 exposes the respective stops acting on the cam hinge member 40. Specifically, it can be seen that stop 60D contacts annular cam surface 90 at end 92. Thus, it can be seen that the extension stop in the outward position limits further extension of the hinge and hence further extension of the brace as it is illustrated in FIG. 1.

Referring to FIG. 6A, the hinge illustrated in 6B is shown in the flexion position. Stop 60B in the radially extended position has limited further flexion of the respective links 22, 24. As can be seen through the top hinge member 44, stop 60B is in the radially outward engaged position.

Referring to FIG. 6B, it can be seen that stop 60B contacts cam surface end 91 of the cam surface 90.

Referring back to FIGS. 3, 5A, 5B, 6A, and 6B, it can be seen that the cam hinge member includes oppositely disposed gun sight exterior markings. A gun sight marking 100 appears at opposite cam end 91. A second gun sight marking appears opposite cam end 92. These respective gun sight markings cooperate with the scales of FIGS. 5A and 6A in enabling setting of the disclosed cam mechanism.

Specifically, a patient under rehabilitation can be asked to flex his knee until physical discomfort occurs. Once the discomfort occurs, the respective gun sight 101 will be registered adjacent a labeled stop in either extension or flexion. At this point, the respective stop nearest the gun sight indicator 100 in the case of extension and 101 in the case of flexion can be moved outwardly for limiting movement of the joint of hinge H. Thus, it can be seen that the respective gun sight indicators 100, 101 cooperate with the imprinted scales to produce rapid setting of the joint.

The reader will understand that FIGS. 5A and 6A illustrate a hinge cap useful for outside of the brace when placed on the left knee or the inside of the brace when placed on the right knee. By reversing the legends for flexion and extension a cap for the inside of the left knee or the outside of the right knee can be produced.

What is claimed is:

1. A hinge for the adjustable restraint of a knee brace having a thigh strut for attachment to the thigh and a calf strut for attachment to the calf, said hinge comprising in combination:

a first hinge member for attachment to said thigh strut for rotation with said thigh strut;

a second hinge member for attachment to said calf strut for rotation with said calf strut;

said first and second hinge members configured for relative rotating engagement one with respect to another to permit said knee brace to flex between flexion and extension limits of knee movement while reinforcing said knee through said thigh strut and calf strut;

one of said hinge members defining an annular cam with respective extension limits and flexion limits for enabling said hinge to be restricted in relative rotation in flexion and extension by stops interior of said cam engaging the respective cam limits;

a plurality of individual radially aligned stops, said stops each having a manipulation portion;

the other of said hinge members defining radially aligned stop ways for permitting toggling movement of said stops with respect to said annular cam between a radially engaged position with respect to said cam limits and a radially disengaged position with respect to said cam limits;

spring means acting between said hinge members and said stops for permitting toggling movement and maintaining position of said stops radially of said hinge between positions engaged to said cam and positions disengaged from said cam; and locking means acting on said stops for locking said stops with respect to said hinge members to maintain the position of said stops with respect to said hinge member.

2. The hinge of claim 1 and wherein said plurality of individually radially aligned stops includes a detent portion, said detent portion acting with said spring means for permitting toggling movement.

3. The invention of claim 1 and wherein said other of said hinge members captures said stops in said radially aligned stops ways.

4. The hinge of claim 3 and wherein said other of said stop members defines a slot overlying each stop for exposing the manipulation portion of each said stop.

5. The invention of claim 4 and wherein said respective slots are labelled for degrees of movement of said hinge.

6. The hinge of claim 5 and wherein said degrees of movement are labelled in flexion and extension.

7. The invention of claim 1 and wherein said locking means includes key means for inhibiting tampering with the setting of said hinge.

8. The invention of claim 4 and wherein one of said portions of said hinge includes a gun-sight indicator for alignment with said defined slots.

9. A knee brace for the adjustable restraint of a knee comprising in combination a thigh strut for attachment to the thigh above the knee;

a calf-strut for attachment to the calf above the knee;

wing means for attachment to said thigh and thigh strut whereby said thigh strut is constrained for movement with the thigh of a wearer;

wing means for attachment to said calf whereby said calf-strut is confined to said calf for movement with the leg of said wearer;

said thigh-strut and calfstrut adjustable with respect to said thigh means and calf means for coinciding respective ends of said strut at the knee of the leg of a wearer;

a hinge for disposition adjacent the knee of a wearer, said hinge including:

a first hinge member for attachment to said thigh strut for rotation with said thigh strut;

a second hinge member for attachment to said calf strut for rotation with said calf strut;

said first and second hinge members configured for relative rotating engagement one with respect to another to permit said knee brace to flex between a flexion and extension limits of knee movement while reinforcing a braced knee through said thigh strut and thigh wings and said calf strut and calf wings;

one of said hinge members defining an annular cam with respective extension limits and flexion limits for enabling said hinge to be restricted in relative rotation in flexion and extension by stops interior of said cam engaging said respective cam limits;

a plurality of individual radially aligned stops, said stops each having a manipulation portion;

the other of said hinge members defining radially aligned stop ways for permitting toggling movement of said stops with respect to said annular cam between a radially engaged position with respect to said cam limits and a radially disengaged position with respect to said cam limits;

spring means acting between said hinge members and stops for permitting toggling movement and maintaining position of said stops radially of said hinge between positions engaged to said cam and positions disengaged from said cam; and locking means acting on said stops for locking said stops with respect to said hinge members to maintain the position of said stop with respect to said hinge member whereby movement of said hinge is restricted.

10. The invention of claim 9 and wherein said paths telescope with respect to said lengths.

11. The invention of claim 9 and wherein and including straps for securing said wings to the thigh and calf of a wearer.

12. The invention of claim 9 and wherein one of said hinge members defined slots for manipulating said stops.

13. The invention of claim 9 and wherein said stops include a detent;

said detent positioned on said stops to coact with said spring means for permitting said stops to toggle between an engaged and disengaged position.

14. The invention of claim 13 and wherein said locking means acts through said spring on said stops.

15. The invention of claim 9 and including a gun sight indicator on one of said hinge members;

said gun sight indicator positioned for alignment with respect to said stops to enable said stops to be set.

16. The invention of claim 9 and wherein said knee brace includes first and second hinge members disposed on either side of said leg;

said knee brace includes first and second struts disposed on either side of said leg and said knee brace includes first and second wings on either side of said knee.

17. A process for the adjustable restraint of a knee brace at a hinge, said hinge having a thigh strut for attachment to the thigh of the leg of a wearer and a calf strut for attachment to the calf of the leg of a wearer, said hinge being positioned coincident to the knee of a wearer;

providing a first hinge member attached to said thigh strut for rotation overlying the knee joint of said patient;

providing a second hinge member for attachment to the calf strut for relative movement with respect to said thigh strut;

providing a hinge coincident to the knee of the wearer, said provided hinge including a cam having a flexion stop and an extension stop on one member of said hinge and a plurality of radially aligned stops affixed to the other member of said hinge;

moving said radially aligned stops into positions of engagement with said cam to limit respective flexion and extension of said knee;

locking said stop members to said said hinge in flexion and extension.

18. The invention of claim 17 and including the step of providing at least one gun sight indicator on one of said hinge members, said gun sight indicator rotating on said hinge member with respect to said stop;

manipulating the joint of said knee to register said gun sight indicator adjacent said stop; and, manipulating said stop to limit knee movement.

* * * * *